United States Patent
Freed

(10) Patent No.: US 6,387,850 B1
(45) Date of Patent: May 14, 2002

(54) PESTICIDE COMPOSITION AND METHOD

(75) Inventor: Brian E. Freed, Lexington, IL (US)

(73) Assignee: Application Technologies, Inc., Lexington, IL (US)

( * ) Notice: Subject to any disclaimer, the term of this patent is extended or adjusted under 35 U.S.C. 154(b) by 0 days.

(21) Appl. No.: 09/157,057

(22) Filed: Sep. 18, 1998

(51) Int. Cl.$^7$ .......................... A01N 25/02; A01N 25/30
(52) U.S. Cl. ...................... 504/358; 514/777; 514/780
(58) Field of Search .......................... 504/358; 514/777, 514/780

(56) References Cited

U.S. PATENT DOCUMENTS

| | | | |
|---|---|---|---|
| 3,360,356 A | 12/1967 | Vartiak | 71/65 |
| 4,107,292 A | 8/1978 | Nemeth | 424/78 |
| 4,363,669 A | 12/1982 | Cottrell et al. | 106/205 |
| 4,404,015 A | 9/1983 | Menon et al. | 71/77 |
| 4,413,087 A | 11/1983 | Bernot | 524/389 |
| 4,510,081 A | 4/1985 | Bronner et al. | 252/603 |
| 4,610,311 A | 9/1986 | Bronner et al. | 169/45 |
| 5,550,224 A | 8/1996 | Hazen | 536/114 |
| 5,658,855 A | 8/1997 | Nalewaja et al. | 504/214 |
| 5,700,759 A | 12/1997 | Caulder et al. | 504/133 |
| 5,703,014 A | 12/1997 | Caulder et al. | 504/142 |
| 5,824,797 A | * 10/1998 | Hazen | 536/114 |

OTHER PUBLICATIONS

O'Sullivan, P. A. et al. "Influence of non–ionic surfactants, ammonium sulphate, water quality and spray volume on the phytotoxicity of glyphosate". Canadian Journal of Plant Science. 61:391–400, Apr. 1981.*

"Salt Antogonism of Glyphosate," John D. Nalawaja and Robert Matysiak, Week Science, 1991, vol. 39:622–628.

"Spray Droplet Residual of Glyphosate in Various Carriers," John D. Nalaewaja, Robert Matysiak, and Thomas P. Freeman, Weed Science, 1992, vol. 40:576–589.

"pH Gets The Acid Test," Farm Journal, Mid–Feb. 1995, p. A–4.

"Characterizing The Impact Of Drift Management Adjuvants On The Dose Transfer Process," Roger A. Downer, et al., Fourth International Symposium on Adjuvants for Agrochemicals, Melbourne, Australia, Oct. 3–6, 1995. (FRI Bulletin No. 193), pp. 138–143.

"Roundup Works Better WithRainwater," Mike Holmberg, Successful Farming, (Jan. 1996), vol. 94, n 1.

"Herbicide Spray Distribution, Quality and Efficacy Interactions: Conlicts in Requirements," R.A. Downer, et al., Aspects of Applied Biology 48, 1997, pp. 79–89.

Performance and Use Guide for ARRAY, No date.

"Hit The Mark," Greg D. Horstmeier, Farm Journal, May –Jun. 1997, pp. 20–21.

Weerasinghe, M.H.G. et al., Journal of the National Science Council of Sri Lanka, (1996) vol. 24, No. 3, pp. 141–157 (Abstract).

Nilsson, H. et al., Rapport, Institutionen for Vaxtodling, Sveriges lantbruksuniversitet, (1984) No. 135, pp. 21–29 (Abstracts).

Downer, R.A. et al., Aspects of Applied Biology, (1997) No. 48, pp. 79–89 (Abstract).

Breeden, G.K. et al., Proc. South Weed Sci. Soc (51 Meet., 276–77, 1998) (Abstract).

Hall, F.R., Phytoparasitica (25, Suppl., 39S–52S, 1997) (Abstract).

Lundegardh, B., Vaxtskyddsnotiser (1994) vol. 58, No. 3, pp. 87–101 (Abstract).

Hallgren, E. et al., Uppsala Meeting, Swedish Crop Protection Conference. Weeds and Weed Control (1991) No. 32, pp. 235–246 (Abstract).

O'Sullivan, P.A. et al., Canadian Journal of Plant Science (1981), vol. 61, No. 2, pp. 394–400 (Abstract).

Selleck, G.W., Proceedings of the Northeastern Weed Science Society, (1980) vol. 34, pp. 281–283 (Abstract).

Kirkland, K.J., Res. Rep. Expert Comm. Weeds West. Can. (39 meet., vol. 2, Suppl. 18, 1992) (Abstract).

* cited by examiner

Primary Examiner—S. Mark Clardy
(74) Attorney, Agent, or Firm—Emrich & Dithmar

(57) ABSTRACT

Application-ready pesticide compositions having enhanced pesticidal efficacy and methods for formulating such compositions are described. Pesticide concentrates are diluted with water purified to have a total dissolved solids content of 1 to about 100 ppm. The resulting application-ready pesticide compositions can be formulated at less than label-specified concentrations and/or applied at less than label-specified volume per area rates without loss of pesticidal efficacy. The application-ready compositions can be substantially free of adjuvants, or they can be optimized using polymer or ammonia based adjuvants to improve dosage transfer. Novel aqueous diluents comprising such adjuvants and low TDS water are also described.

39 Claims, No Drawings

PESTICIDE COMPOSITION AND METHOD

FIELD OF INVENTION

This invention relates to an improved pesticide composition and methods for its preparation and use. More specifically, this invention is directed to the use of purified water having low total dissolved solids for preparing application-ready pesticide compositions from pesticide concentrates. The use of purified water, optionally in combination with art-recognized polymer adjuvants and/or ammonia or ammonium salts, to formulate application-ready pesticide compositions provides enhanced pesticidal efficiency and efficacy with concomitant reduction in crop injury.

BACKGROUND AND SUMMARY OF THE INVENTION

The use of pesticides, including both herbicides and insecticides, is an essential component of commercial farming operations. The presence of crop consuming insects and nutrient consuming weeds not only work to decrease crop yields, but infestations of such pests also leads to reduced crop quality. The use of pesticides in agricultural production has therefore become an essential aspect of commercial farming protocols. Yet the use of such pesticides is not without recognized disadvantages. The inherent phytotoxic activity of herbicides can lead to crop damage and reduced yield. Moreover, the environmental community is becoming more intolerant of increasing pesticide levels in rivers and streams due to "run-off" from pesticide treated crop areas.

Accordingly, there has been a significant research and development effort directed to improving pesticide efficiency generally and for crop-specific and/or target species-specific applications. Numerous adjuvants for preparing application-ready pesticide formulations have been developed and utilized commercially. Such adjuvants are typically combined with the active pesticide component(s) during preparation of the application-ready (tank mix) pesticide formulations. Such formulations are typically prepared from pesticide concentrates, each having label or package insert instructions for dilution with water to a prescribed concentration, often crop-dependent or target pest species-dependent, for application to crop areas infested with said species, at a prescribed, predetermined volume or weight per area rate. Such compositions are typically designated for pre-emergent or post-emergent application and they can be applied as a spray, injected into the soil, or wiped from a bar mounted wick directly onto the target plant species.

Many adjuvants have been developed with the goal of improving performance of aqueous pesticide formulations. Such adjuvants include surfactants which promote the spreading and retention of applied pesticide formulations on target plant species. Other adjuvants are detailed for minimizing the known deleterious efforts of water hardness on pesticide performance. Ammonia or ammonium salts have been used for improved pesticide uptake and various art-recognized agriculturally acceptable polymers are detailed for controlling size, drift and surface adherence of droplets as they are applied to crop areas. While the use of adjuvants for agricultural pesticide formulations provide advantage in numerous specific applications, their efficacy is significantly dependent on the species of pesticide, the source of water for diluting the commercial pesticide concentrate, the use of other adjuvants used in combination, and weather and soil conditions at the time of application and post-application. Further, the use of chemical adjuvants add to the crop management costs, and, like the pesticides they are intended to complement, adjuvants can themselves provide basis for additional concern from an environmental conservation perspective.

The present invention relates to novel pesticidal formulations which exhibit enhanced pesticidal efficacy without or with but selective use of art-recognized agricultural pesticide adjuvants. Most, if not all, commercial agricultural pesticides are provided as pesticide concentrates having label or package insert instructions for dilution with water to a prescribed concentration. The prescribed concentration is often dependent on the target test species and/or the crop species being treated to manage pest infestation. The label or package insert instructions for pesticide concentrates typically prescribe, as well, an application rate (volume of the diluted application-ready pesticide formulation per unit area of the locus of application to provide a predetermined weight of pesticide per acre).

In accordance with the present invention, the use of purified water to dilute pesticide concentrates provide application-ready pesticide formulations which exhibit enhanced pesticidal efficacy and when applied to the locus of crops, reduced crop damage. Water utilized to prepare application-ready pesticide compositions in accordance with this invention is purified to have a total dissolved solids (TDS) content of 1 to about 100 ppm. The resulting aqueous pesticide composition is characterized by enhanced pesticidal efficiency and reduced crop damage and therefore provides a greater margin for variability in application rate (volume or weight per unit area) during use of the pesticide formulation.

The improved pesticidal efficiency of application-ready pesticide formulations (tank mixes) prepared by diluting pesticide concentrates with purified water in accordance with this invention is such that the pesticide concentrate can be diluted with up to four times the volume of water appropriate to provide the prescribed concentration (where the application-ready tank mix is applied at the volume/acre rate specified for the prescribed concentration). Alternatively, or in addition, the present application-ready pesticide compositions can be applied at less than the predetermined volume per application area rate without compromise of pesticidal efficacy. Thus, regardless of how the pesticide is delivered/applied, the present invention allows it to be used at a less-than-label rate to the locus of target pest species without compromise of pesticidal efficacy.

While one object of this invention is to provide effective pesticidal formulations without use of costly adjuvants, it has been found that there are at least two art-recognized adjuvant classes that can be utilized to complement the efficiency realized with the use of low TDS water as a pesticide diluent in accordance with this invention: polymers which work to control droplet size, surface affinity, drift and drying, and ammonia or ammonium salts which are believed to work to enhance plant membrane transport of the pesticide.

Thus, in accordance with another embodiment of the invention there is provided an aqueous composition useful as a diluent for pesticidal concentrates to improve pesticidal efficiency and improve pesticidal performance, said composition consisting essentially of a mixture of purified water having 1 to about 100 ppm total dissolved solids and a water dispersible polymer at a concentration of about 0.075 to about 0.2% by weight per unit volume. Such aqueous composition can be formulated to include, as well, ammonia or an ammonium salt at a concentration of about 0.5 to about 4% by weight ammonia per unit volume, In a related embodiment there is provided an aqueous composition for use as a diluent for pesticide concentrates to enhance pesticidal efficiency of said pesticides wherein the composition consists essentially of a mixture of purified water having 1 to about 100 ppm total dissolved solids an ammonia or an ammonium salt at a concentration of about 0.5 to about 4% by weight ammonia per unit volume.

Another related embodiment of the invention is based on use of certain commercially available polymer adjuvants, particularly optionally derivatized polygalactomannans in aqueous pesticide compositions diluted in water to a concentration less than the prescribed concentration without loss of pesticidal efficacy. Polygalactomannans are the natural polymer components of plant derived gum; for example, gums derived from guar and tamarind. The use of guar gums as a drift control agent in pesticidal compositions is described and claimed in U.S. Pat. No. 5,550,224 the disclosure of which is expressly incorporated by reference. Such pesticide polygalactomannan formulations can also be formulated to include ammonia or an ammonium salt so that the composition includes about 0.5% to about 4% by weight ammonia per unit volume. Preferably the water used to dilute the pesticide concentrate is purified water having a total dissolved solids of 1 to about 100 ppm.

In an alternative, but related embodiment of the invention there is provided a method for improving crop coverage efficiency of a pesticide concentrate composition having label (or package insert) instructions for dilution with water to a crop dependent or a pest species-dependent concentration and a recommended volume per area application rate. The method includes the steps of diluting the pesticide concentrate with at least the label specified volume of water, adding about 0.5 to about 2.0 lbs. of an optionally derivatized polygalactomannan composition per 100 gallons of water used to, and applying the diluted pesticide composition to the locus of crops at less than the recommended volume per acre so that the application rate per acre of the pesticide is less than 95% of the label-specified application rate.

DETAILED DESCRIPTION OF THE INVENTION

There is provided in accordance with the present invention improved pesticide compositions and their preparation and use. The invention is based on the discovery that the use of water purified to reduce total dissolved solids content (TDS) as the diluent for pesticide tank mixes results in significant enhancement in pesticidal efficiency. It has been found that water meeting such purity specifications can be provided at an economical cost for agricultural use using any of a wide variety of art recognized purification techniques including ultra-filtration, deionization, reverse osmosis, or nanofiltration, alone or in combination with other art recognized water purification techniques. One preferred method for producing water having the requisite degree of purity for use in accordance with this invention is reverse osmosis (RO). In one embodiment of the invention, the low TDS water is produced by reverse osmosis treatment of a water source that had been subjected to a pretreatment selected from the group consisting of carbon filtration, softening to reduce divalent metal ion concentration, or chemical dosing. RO water can be produced, delivered and stored in the high volume amounts required for preparation of pesticidal formulations (tank mixes) in farming operations, and it can be provided at an economically acceptable price for commercial agriculture use. The purified water can be typically stored in polymer, stainless steel, fiberglass or glass-lined vessels to maintain water quality until use. The purified water can be further treated with, for example ozone, algicides, bactericides, or bacteriostats in concentrations effective to prevent unwanted contamination during water storage.

The purified water used to formulate the improved pesticide compositions of the present invention preferably has a total dissolved solids level of 1 to about 100 ppm, more preferably about 1 to about 75 ppm, most preferably about 1 to about 50 ppm. Commercially produced RO water typically contains about 5 to about 50 ppm dissolved solids. Distilled water theoretically has zero ppm TDS. While it could be used to achieve enhanced pesticidal efficacy in accordance with this invention, the costs of producing it effectively prohibits its use in high volume agricultural operations.

The water specified for use in accordance with the invention can be mixed with one or more selected adjuvants that have been found to complement pesticidal efficiency of pesticide tank mix compositions formulated using low TDS water. Thus, for example, in one embodiment of the invention there is provided an aqueous composition for use a diluent for pesticide concentrates to enhance the pesticidal efficiency of said concentrates. The composition consists essentially of a mixture of low TDS water (1 to about 100 ppm total dissolved solids) and a water dispersible polymer at a concentration of about 0.075 to about 0.2% by weight per unit volume. The polymer added for formulating the aqueous diluent and/or aqueous pesticide compositions in accordance with this invention can be any agriculturally acceptable polymer adjuvant. Polymers currently commercially available include the viscoelastic polyacrylamides, polyethylene oxides, and poly (vinyl pyrrolidones) and derivatized polygalactomannans. (See U.S. Pat. Nos. 4,413,087 and 5,550,224, for example). In one preferred embodiment, the polymer is an optionally derivatized polygalactomannan. The underivatized polygalactomannan is a natural polymer typically obtained guar or tamarind. In another embodiment an aqueous diluent for pesticide concentrates can be prepared by combining low TDS purified water with ammonia or ammonium salt at a concentration of about 0.5 to about 4% by weight ammonia per unit volume. Alternatively, an aqueous pesticide diluent can be prepared for use in accordance with this invention by combining low TDS water with both a water dispersible polymer and ammonia or an ammonium salt each at a concentration within the above mentioned respective concentration ranges. The aqueous diluent compositions can, as discussed above with respect to the purified water itself, can be treated with an effective amount of one or more bactericides, algicides, or bacteriostats. Further, storage vessels for such diluent formulations can be fitted with an ozonator to provide antimicrobially effective concentrations of ozone in the stored aqueous diluent.

In one embodiment of the invention there is provided a method for enhancing the efficacy of pesticide against a target pest species. Agricultural pesticides are typically provided as water dilutable pesticide concentrates having label instructions for dilution with water to a prescribed concentration, typically target species or coop-species dependent, for application to areas infested with that species at a predetermined prescribed volume or weight per area rate. The pesticide concentrate is diluted in accordance with this invention with a volume of purified water having 1 to about 100 ppm total dissolved solids, wherein the volume of water is at least sufficient to provide an application-ready pesticide tank mix formulation having a concentration equal to the prescribed concentration. Alternatively, one of the above described aqueous diluent compositions containing either an adjuvant polymer or ammonia/ammonium salt (or both) can be substituted for the low TDS water. Alternatively, the polymer or ammonia/ammonium salt components can be added with the low TDS water during formulation of the application-ready composition.

In a preferred embodiment of the method of this invention the volume of the purified aqueous diluent (either purified water alone or in combination with polymer or ammonia/ammonium salt) used to dilute a pesticide concentrate to prepare a application-ready pesticide composition exceeds the amount necessary to provide the concentration prescribed for the target test species. In fact, it has been found that up to 400% of the volume of water appropriate to provide the prescribed concentration can be added to the pesticide concentrate with little detectable loss of pesticide efficacy when such applications are applied at the label specified tank mix volume per acre rate. In another aspect of this invention, an application-ready pesticide composition prepared by diluting a pesticide concentrate with purified water (or water diluent composition as discussed above) can be applied to areas infested with the target pest species at a rate less than the predetermined (label-specified) rate. Indeed, tank mix formulations prepared by diluting a pesticide concentrate with a volume of purified water greater than the label specified volume can be applied at less than the label specified volume per acre rate with little, if any, loss of pesticidal efficacy.

The application-ready tank mix pesticide compositions in accordance with this invention can be formulated for application to crops or to other areas of insect or weed infestation requiring pesticidal treatment. In one preferred embodiment of the invention the pesticidal compositions are used to treat pest infestation in the locus of crops. The use low TDS water in accordance with this invention to prepare pesticide compositions for such agricultural use, not only enables cost savings in the form of reduced usage of pesticide concentrates (and reduced chemicals released into the environment), but it also provides reduced crop damage. Moreover, use of the low TDS water to formulate application ready pesticide compositions in accordance with this invention allows good crop coverage efficiency without the use of the many art recognized adjuvants such as surfactants, crop oils, chelating agents, wetting agents and the like without compromise of pesticidal efficacy. The reduction in adjuvant use enabled by use of the present invention offers not only economic advantage but as well inherent advantage to the local environment.

The method and compositions of the present invention find application for improvement in treatment efficiency of both post-emergent and pre-emergent herbicides and pesticides. The invention finds particular utility, however, in the application of post-emergent herbicides both in species specific (selective) crop treatment applications and in species nonspecific (broad range) herbicide applications such as vegetation reduction in fence rows and rights of way. Examples of herbicide concentrates can be used in the present method and composition embodiments of the invention include but are not limited to: ACCENT® (nicosulfuron, DuPont), ATRAZINE® (Atrazine), BANVEL® (dicamba, Sandoz), BASAGRAN® (bentazon, BASF), BASIS® (rimsulfuron and thifensulfuron, DuPont), CLARITY® (dicamba, Sandoz), MARKSMAN® (dicamba and atrazine), PINNACLE® (thifensulfuron, DuPont), POAST PLUS® (sethoxydim, BASF), PROWL® (pendimethalin, American Cyanamid), PURSUIT PLUS® (pendimethalin and imazethapyr, American Cyanamid), REFLEX® (fomesafen), RESOLVE® (imazethapyr and dicamba, American Cyanamid), ROUNDUP® (glyphosate, Monsanto), BLAZER® (acifluorifin, BASF), LIBERTY® (glufossinate, AgrEvo), TOUCHDOWN® (sulfosate, Zeneca), 2,4D® and 2,4 DB® and tank mix blends of such pesticides (and others).

The mechanism by which the use of low TDS water in pesticide formulations provide the observed enhanced pesticidal efficacy is still not fully understood. It is likely that there are several physical and chemical factors that are working together to provide apparent enhanced dosage transfer efficiency (in the target species) without increase in crop injury. One possible explanation of the enhanced dosage transfer efficiency deriving from use of the invention focuses on both the chemistry and physics of the drying of droplets of the aqueous pesticide composition on the surface of the target species. Uptake of the pesticide into the target species (systemically) is believed to be a necessary antecedent of pesticidal efficacy. Enhancing the efficiency of systemic delivery, i.e., the dosage transfer efficiency of the active pesticide, enhances pesticidal efficacy. In pesticide compositions formulated using typical high TDS water (e.g., well water) the solids content of the water precipitates on the surface of the leaf during the later stages of droplet drying. It is believed that the deposition of the solids content (salts) of the drying droplet on the leaf serves to insulate the leaf surface from the pesticidal composition at a point in the drying process where the pesticide concentration (and thus the concentration gradient between the droplet residue and the leaf surface) is the greatest. The solids deposited on the leaf's surface during the later stages of droplet drying thus serve to "insulate" the leaf's surface from the droplet residue at a point in time when the concentration gradient influenced dosage transfer potential is the greatest, i.e. during the period of time where the last liquid portions of the droplet are drying on the surface of the target species. Further the forming salt crystals effectively provide a high surface area for holding the pesticide composition (deposited from the drying droplet) away from the surface of the pest species. Minimizing the concentration of dissolved solids in the applied pesticide composition minimizes the deposit of surface insulating salts on the surface of the target species thereby resulting in enhanced dosage transfer into the target species. It is also speculated that the increasing solids/salt concentration in the drying droplet can also work to interfere with both the chemical and physical aspects of dosage transfer, i.e. the systemic delivery of surface applied pesticide. As the concentration of solids/salts in the drying droplet become greater than that in the surface tissues of the target species, osmotic pressure can theoretically work against dosage transfer. That phenomenon can be minimized by use of the low TDS pesticide compositions in accordance with this invention.

As discussed above, it has been found that the use of polymer adjuvant, preferably a polygalactomannan derived from guar or tamarind, further enhances the pesticidal efficacy of the low TDS pesticide compositions of this invention. That polymer is currently commercially available for agricultural use as a drift control agent sold under the trade name DR 2000®. The polymer is also a component of a crop spray adjuvant sold under the trade name "Array®," an adjuvant that is detailed for improving spray retention, increasing spray penetration, and creating a more uniform spray droplet to deliver more herbicide on the target species.

Such guar gum (polygalactomannan) containing adjuvant compositions have been found to improve pesticidal efficacy in the present low TDS pesticide compositions. It is believed that the polymer component not only works to improve droplet uniformity and retention on the surface as previously reported, but it also retards the rate of droplet evaporation thereby prolonging the period of time that the leaf surface is in contact with the evaporating spray droplets of ever increasing pesticide concentration. In other words, by retarding the rate of droplet evaporation the polymer can work to enhance the dosage transfer rate by prolonging the period of contact of the drying droplet with the surface of the target species. Thus, use of polymer adjuvants such as vegetable gums, including particularly optionally derivatized galactomannans, such as those described and claimed in U.S. Pat. No. 5,550,224, expressly incorporated herein by reference, can work to enhance dosage transfer rate using effective amounts of the polymer in application-ready pesticide compositions the pesticide concentration itself can be reduced to less than 95% of the label-specified species-dependent or crop-dependent pesticide concentration without any loss of pesticidal efficacy.

Thus, in accordance with another aspect of the invention there is provided an aqueous pesticide composition prepared by the dilution of a pesticide concentrate having label instructions for dilution with water to a prescribed crop-dependent or pest-species-dependent concentration. The aqueous pesticide composition comprises the pesticide concentrate diluted with water to a concentration less than the prescribed concentration and optionally derivatized polygalactomannan in an amount of about 0.075 to about 0.2% by weight per unit volume of the pesticide composition. In one embodiment the aqueous pesticide composition is prepared by diluting the pesticide concentrate to a concentration less than or equal to 95% of the prescribed concentration without loss of pesticidal efficacy when applied at the specified tank mix application rate. In another embodiment the pesticide concentrate is diluted to a concentration of about 50 to about 95% of the prescribed concentration without loss of pesticide efficacy when applied to the locus of a target test species at a tank mix volume per area rate no greater than the label specified rate. Accordingly, crop coverage efficiency of a pesticide concentrate composition can be increased by using reduced concentration of the pesticide in application-ready pesticide compositions in combination with an optionally derivatized polygalactomannan. Typically, the galactomannan is added to the diluted application-ready pesticide composition at a rate of about 0.5 pounds to about 2 pounds for each 100 gallons of water used to form the application-ready pesticide composition. The resulting tank mix composition is applied, typically by spraying, at a volume per acre rate not more than the label-recommended volume per acre rate (i.e., that specified for a species-dependent or crop-dependent pesticide concentration). In one preferred embodiment of the invention the water used to dilute the pesticide concentrate is purified to have a total dissolved solids of 1 to about 100 ppm. In another embodiment the crop application-ready pesticide composition can be formulated to include ammonia or an ammonium salt so that the composition includes about 0.5% to about 4% by weight ammonia per unit volume.

The advantage of enhanced dosage transfer using optionally derivatized polygalactomannan as a crop spray adjuvant can also be realized by formulating the application ready pesticide composition to the label specified pesticide concentration and thereafter applying that composition at less than the recommended volume per acre. Preferably the water used to dilute the pesticide concentrate is purified to have a total dissolved solids of about 1 to about 100 ppm, more preferably about 1 to about 50 ppm, most typically about 5 to about 20 ppm. Further enhancement of pesticidal efficiency can be achieved, as with other embodiments of the invention by formulating the application ready composition to include ammonia or ammonium salt of an organic or inorganic acid so that the composition includes about 0.5 to about 4% by weight ammonia per unit volume.

Evaluation of Demineralized Water Spray Solution For Improved Consistency of Pesticide Performance Introduction: The study conducted is a formalized experiment which valuates the potential of improved efficacy of pesticides by the use of demineralized water spray solution. Current water spray solutions are not processed in order of achieved quality levels as being evaluated in this study. Previous studies have proven that mono and divalent ions minerals such as calcium and magnesium that are natural in water sources effect pesticide efficiency of dosage application, deposition, absorption, translocation and efficacy. By minimizing the mineral content in the water spray solution then pesticide performance should be more consistent.

Materials and Methods: Applications were made to glyphosate-tolerant soybeans on Jun. 10, 1998. Weed species present ranging in height from 5 to 20 cm included giant foxtail (*Setaria faberii*), barnyard grass (*Echinochloa crus-galli*), volunteer corn (*Zea mays*) and yellow foxtail (*Setaria glauca*) Treatments were applied using Spraying Systems Turbo TeeJet TT-11002 nozzles spaced 50 cm apart on the spray boom at 207 kPa spray pressure resulting in a spray volume application of 1897 liters per hectare.

Spray solutions consisted of two comparison levels of mineral hardness as measured by TDS in ppm. The original solution consisted of 10 ppm. The second solution measuring 400 ppm was established using calcium chloride at approximately 227 grams per 378 liters.

Herbicide applications of glyphosate in form of Roundup Ultra® (Monsanto Company) formulation were applied at four rates: 26, 53, 105 and 210 grams of acid equivalent per hectare (g ae/ha) A spray adjuvant, Array® at 4 kilograms per 378 liters of spray solution was added to the spray solution prior to the addition of the herbicide. Array was evaluated across herbicide and spray solution treatments. Array consists of a micro-homogenized combination of AMS (ammonium sulfate) fertilizer at 94.4% analysis 21-0-0-24 (nitrogen-phosphorus-potassium-sulfur) and DR 2000 (Rhodia Surfactants) at 5.6%, a short-chain guar-based polymer.

Results and Discussion: Herbicide efficacy was improved across all weed species tested by using the higher quality water spray solution. The 10 ppm TDS water solution required approximately 50% of the herbicide dosage as compared to the 400 ppm TDS water solution to achieve similar weed efficacy results. The addition of Array slightly improved week control, but was not a comparable replacement for a higher quality water spray solution.

TABLE 1

Glyphosate Applied with Two Levels of Water Spray Solution Quality

| Treatment | Glyphosate (g ae/ha) | Solution TDS (ppm) | Array 4 kg/ 378 L | Giant Foxtail | Barnyard Grass | Volunteer Corn | Yellow Foxtail |
|---|---|---|---|---|---|---|---|
| 1 | 26 | 10 | No | 2 | 2 | 1 | 2 |
| 2 | 53 | 10 | No | 3 | 4 | 3 | 3 |
| 3 | 105 | 10 | No | 6 | 5 | 5 | 5 |
| 4 | 210 | 10 | No | 9 | 9 | 9 | 8 |
| 5 | 26 | 10 | Yes | 3 | 3 | 2 | 2 |
| 6 | 53 | 10 | Yes | 4 | 5 | 4 | 4 |
| 7 | 105 | 10 | Yes | 8 | 7 | 8 | 7 |
| 8 | 210 | 10 | Yes | 10 | 10 | 10 | 9 |
| 9 | 26 | 400 | No | 0 | 0 | 0 | 0 |
| 10 | 53 | 400 | No | 1 | 1 | 1 | 1 |
| 11 | 105 | 400 | No | 2 | 2 | 2 | 2 |
| 12 | 210 | 400 | No | 5 | 5 | 5 | 5 |
| 13 | 26 | 400 | Yes | 1 | 1 | 1 | 1 |
| 14 | 53 | 400 | Yes | 2 | 2 | 2 | 2 |
| 15 | 105 | 400 | Yes | 3 | 3 | 3 | 3 |
| 16 | 210 | 400 | Yes | 6 | 6 | 6 | 5 |

Visual Ratings taken July 3, 1998, 23 days after application
Scale: 0 = No weed control, 10 = complete weed control

What is claimed:

1. An improved pesticide composition comprising
a water dilutable pesticide concentrate having an optionally derivatized polygalactomannan in an amount of about 0.075 to about 0.2% by weight per unit volume, and
a volume of water purified by reverse osmosis to have a total dissolved solids of at least 1 to about 100 ppm.

2. The improved pesticide composition of claim 1 further comprising a water dispersible polymer so that it is present in the diluted pesticide composition at about 0.075 to about 0.2% by weight per unit volume.

3. The improved pesticide composition of claim 2 further comprising ammonia or an ammonium salt of an organic or inorganic acid so that the diluted pesticide composition includes about 0.5 to about 4% by weight ammonia per unit volume of the pesticide composition.

4. The improved pesticide composition of claim 1 further comprising ammonia or an ammonium salt so that the diluted pesticide composition includes about 0.5 to about 4% by weight ammonia per unit volume of the pesticide composition.

5. The improved pesticide composition of claim 1 wherein the water purified by reverse osmosis is subjected to a pretreatment selected from the group consisting of carbon filtration, softening to reduce divalent metal ion concentration, and chemical dosing.

6. The improved pesticide composition of claim 1 wherein the purified water used to dilute the pesticide concentrate includes an effective amount of an algicide or a bactericide.

7. The improved pesticide composition of 1 wherein the optionally derivatized polygalactomannan is obtained from guar or tamarind.

8. The improved pesticide composition of claim 1 substantially free of any crop spray adjuvants.

9. An aqueous pesticide composition prepared by dilution of a pesticide concentrate, said aqueous pesticide composition comprising said pesticide concentrate diluted with water purified by reverse osmosis to have about 1 to about 100 ppm total dissolved solids and an optionally derivatized polygalactomannan in an amount of about 0.075 to about 0.2% by weight per unit volume.

10. An aqueous composition for use as a dilutant for pesticide concentrates to enhance the pesticidal efficacy of said pesticides, said composition consisting essentially of a mixture of water purified by reverse osmosis to have about 1 to about 100 ppm total dissolved solids and an optionally derivatized polygalactomannan at a concentration of about 0.075 to about 0.2% by weight per unit volume.

11. An aqueous composition for use as a dilutant for pesticide concentrates to enhance the pesticidal efficacy of said pesticides, said composition consisting essentially of a mixture of water purified by reserve osmosis to have about 1 to about 100 ppm total dissolved solids, an optionally derivatized polygalactomannan at a concentration of about 0.075 to about 0.2% by weight per unit volume, and ammonia or an ammonium salt at a concentration of about 0.5 to about 4% by weight ammonia per unit volume.

12. An aqueous composition for use as a dilutant for pesticide concentrates to enhance the pesticidal efficiency of said pesticides, said composition consisting essentially of a mixture of water purified by reverse osmosis to have about 1 to about 100 ppm total dissolved solids, an optionally derivatized polygalactomannan in an amount of about 0.075 to about 0.2% by weight per unit volume, and ammonia or an ammonium salt at a concentration of about 0.5 to about 4% by weight ammonia per unit volume.

13. The aqueous composition of claim 10, 11, or 12 wherein the purified water component of said compositions has a total dissolved solids of 1 to about 50 ppm.

14. A process for preparing an improved aqueous pesticide composition for application to a locus of crops, the use of said improved composition characterized by enhanced pesticidal efficacy and reduced crop damage, said composition comprising a pesticide concentrate and an amount of water sufficient to dilute the concentrate to a predetermined pesticide concentration, said improved process comprising diluting the pesticide concentrate with water purified by reverse osmosis to have a total dissolved solids of 1 to about 100 ppm and adding to the diluted pesticide concentrate an optionally derivatized polygalactomannan in an amount of about 0.075 to about 0.2% by weight per unit volume.

15. A method for enhancing the efficacy of a pesticide against a target pest species, said pesticide being provided as a water dilutable pesticide concentrate for application as a water diluted solution of said pesticide to areas infested with said target pest species at a predetermined volume per area rate, said method comprising diluting the pesticide concentrate with a volume of water purified by reverse osmosis to have 1 to about 100 ppm total dissolved solids, adding to the diluted pesticide an optionally derivatized polygalactomannan in an amount of about 0.075 to about 0.2% by weight per unit volume and applying said diluted pesticide to areas infested with said target pest species.

16. The method of claim 15 comprising adding ammonia or an ammonium salt so that the diluted pesticide formulation includes about 0.5 to about 4% by weight ammonia per unit volume of the pesticide formulation.

17. The method of claim 16 wherein the purified water used to dilute the pesticide concentrate has about 1 to about 20 ppm total dissolved solids.

18. The method of claim 15 comprising adding ammonia or an ammonium salt so that the diluted pesticide formulation includes about 0.5 to about 4% by weight ammonia per unit volume of the pesticide formulation.

19. The method of claim 15, 16 or 18 wherein the purified water used to dilute the pesticide concentration has about 1 to about 50 ppm total dissolved solids.

20. The method of claim 15, 16, or 18 wherein the water purified by reverse osmosis is subjected to a pretreatment selected from the group consisting of carbon filtration, softening to reduce divalent metal ion concentration, and chemical dosing.

21. The method of claim 15 wherein the purified water used to dilute the pesticide concentrate has about 1 to about 20 ppm total dissolved solids.

22. The method of claim 15 further comprising the step of applying the pesticide formulation to areas infested with the target pest species at the predetermined rate.

23. The method of claim 15 further comprising the step of applying the pesticide formulation to areas infested with the target pest species at a rate less than the predetermined rate.

24. The method of claim 15 wherein the purified water used to dilute the pesticide concentrate includes an effective amount of an algicide or a bactericide.

25. The method of claim 15 wherein the optionally derivatized polygalactomannan is derived from guar or tamarind.

26. A method for enhancing the pesticidal efficacy of and reducing crop damage from a pesticide composition comprising a water diluted pesticide concentrate applied to the locus of crops infested with a target pest species at a prescribed volume per area rate, said method comprising diluting the pesticide concentrate with a volume of water purified by reverse osmosis to have a total dissolved solids of 1 to about 100 ppm, adding to the diluted pesticide formulation an optionally derivatized polygalactomannan in an amount of about 0.075 to about 0.2% by weight per unit volume, and applying said formulation to the locus of said crops at a volume per area rate up to the prescribed rate for the target pest species.

27. The method of claim 26 wherein the pesticide composition is applied to the locus of crops at a rate less than the prescribed rate for the target pest species.

28. The method of claim 26 or 27 wherein the water purified by reverse osmosis is subjected to a pretreatment selected from the group consisting of carbon filtration, softening to reduce divalent metal ion concentration, and chemical dosing.

29. The method of claim 26 further comprising adding ammonia or an ammonium salt of an organic or inorganic acid so that the diluted pesticide formulation includes about 0.5 to about 4% by weight ammonia per unit volume of the pesticide formulation.

30. The method of claim 29 wherein the purified water used to dilute the pesticide concentrate has about 1 to about 20 ppm total dissolved solids.

31. The method of claim 26 further comprising adding ammonia or an ammonium salt so that the diluted pesticide formulation includes about 0.5 to about 4% by weight ammonia per unit volume of the pesticide formulation.

32. The method of claim 26, 27, 29, or 31 wherein the purified water used to dilute the pesticide concentration has about 1 to about 50 ppm total dissolved solids.

33. The method of claim 26 wherein the purified water used to dilute the pesticide concentrate has about 1 to about 20 ppm total dissolved solids.

34. The method of claim 26 wherein the pesticide composition is substantially free of crop spray adjuvants.

35. The method of claim 26 wherein the pesticide composition is applied to areas infested with the target pest species at a rate less than 50% of the predetermined rate.

36. The method of claim 26 wherein the purified water used to dilute the pesticide concentrate includes an effective amount of an algicide or a bactericide.

37. The method of claim 26 wherein the optionally derivatized polygalactomannan is obtained from guar or tamarind.

38. A method for improving the crop coverage efficiency of a pesticide concentrate composition applied as a diluted pesticide composition at a recommended volume per area rate, said method comprising the steps of diluting the pesticide concentrate composition with water purified by reverse osmosis to have about 1 to about 100 ppm total dissolved solids, adding about 0.5 lbs. to about 2.0 lbs. of an optionally derivatized polygalactomannan per 100 gallons of water to form a crop application-ready pesticide composition, and applying the crop application-ready pesticide composition at not more than the recommended volume per area rate.

39. The method of claim 38 further comprising the step of adding ammonia or an ammonium salt to the crop application-ready pesticide composition so that the composition includes about 0.5% to about 4% by weight ammonia per unit volume.

* * * * *